US007896877B2

(12) United States Patent
Hall et al.

(10) Patent No.: US 7,896,877 B2
(45) Date of Patent: Mar. 1, 2011

(54) SURGICAL INSTRUMENT

(75) Inventors: Matthew R. Hall, Reading (GB); Mark G. Marshall, Winnersh (GB); Colin C. O. Goble, South Oxfordshire (GB); Francis Amoah, Cardiff (GB); Kelvin J. Varney, Monmouthshire (GB); Julian Mark Ebbutt, Marshfield (GB)

(73) Assignee: Gyrus Medical Limited, Cardiff (GB)

( * ) Notice: Subject to any disclaimer, the term of this patent is extended or adjusted under 35 U.S.C. 154(b) by 1070 days.

(21) Appl. No.: 11/132,436

(22) Filed: May 19, 2005

(65) Prior Publication Data

US 2005/0261677 A1   Nov. 24, 2005

Related U.S. Application Data

(63) Continuation-in-part of application No. 10/924,954, filed on Aug. 25, 2004, now abandoned.

(30) Foreign Application Priority Data

May 20, 2004 (GB) .................................. 0411270.2

(51) Int. Cl.
*A61B 18/14* (2006.01)
(52) U.S. Cl. ......................................................... 606/48
(58) Field of Classification Search .................. 606/41, 606/45–52
See application file for complete search history.

(56) References Cited

U.S. PATENT DOCUMENTS

| 5,197,968 | A | 3/1993 | Clement |
| 5,215,521 | A | 6/1993 | Cochran |
| 5,304,124 | A | 4/1994 | Essig et al. |
| 5,336,237 | A | 8/1994 | Chin et al. |
| 5,342,315 | A | 8/1994 | Rowe |
| 5,439,474 | A | 8/1995 | Li |
| 5,443,472 | A | 8/1995 | Li |
| 5,520,634 | A | 5/1996 | Fox et al. |
| 5,562,694 | A | 10/1996 | Sauer et al. |
| 5,569,284 | A | 10/1996 | Young et al. |

(Continued)

FOREIGN PATENT DOCUMENTS

DE    43 12 147 A1    10/1993

(Continued)

OTHER PUBLICATIONS

International Search Report in International Application No. PCT/GB2007/003292, mailed Mar. 17, 2008, corresponding to related U.S. Appl. No. 11/523,807.

(Continued)

*Primary Examiner* — Lee S Cohen
(74) *Attorney, Agent, or Firm* — Nixon & Vanderhye P.C.

(57) ABSTRACT

A device for morcellating tissue within a body cavity of a patient comprises a stationary tube having a distal end portion, and a bipolar electrosurgical electrode assembly located at the distal end of the tube. The electrosurgical electrode assembly comprises first and second electrodes separated by an insulation member, the bipolar electrosurgical electrode assembly extending around the circumference of the distal edge of the tube. When an electrosurgical cutting voltage is applied to the electrode assembly, and relative movement is initiated between the tube and the tissue, a core of severed tissue is formed within the tube such that it can be removed from the body cavity of the patient. A tissue-pulling device such as a jaw assembly can be employed to pull tissue against the distal end of the tube.

26 Claims, 8 Drawing Sheets

U.S. PATENT DOCUMENTS

| | | | |
|---|---|---|---|
| 5,618,296 | A | 4/1997 | Sorensen et al. |
| 5,669,927 | A | 9/1997 | Boebel et al. |
| 5,746,760 | A | 5/1998 | Humphrey, Jr. |
| 5,843,040 | A | 12/1998 | Exline |
| 5,916,230 | A | 6/1999 | Brenneman et al. |
| 5,957,884 | A | 9/1999 | Hooven |
| 5,980,544 | A | 11/1999 | Vaitekunas |
| 6,007,512 | A | 12/1999 | Hooven |
| 6,024,751 | A | 2/2000 | Lovato et al. |
| 6,036,681 | A | 3/2000 | Hooven |
| 6,039,748 | A | 3/2000 | Savage et al. |
| 6,045,566 | A | 4/2000 | Pagedas |
| 6,083,177 | A | 7/2000 | Kobren et al. |
| 6,156,049 | A | 12/2000 | Lovato et al. |
| 6,159,179 | A | 12/2000 | Simonson |
| 6,162,235 | A | 12/2000 | Vaitekunas |
| 6,231,591 | B1 | 5/2001 | Desai |
| 6,251,121 | B1 | 6/2001 | Saadat |
| 6,468,228 | B1 | 10/2002 | Topel et al. |
| 6,564,107 | B1 * | 5/2003 | Bodner et al. ............ 607/122 |
| 6,773,432 | B1 * | 8/2004 | Clayman et al. ............ 606/41 |
| 2003/0149442 | A1 | 8/2003 | Gellman et al. |
| 2005/0070892 | A1 | 3/2005 | Ciarrocca |

FOREIGN PATENT DOCUMENTS

| | | |
|---|---|---|
| DE | 44 40 035 A1 | 5/1996 |
| EP | 0 357 339 A2 | 3/1990 |
| EP | 0 424 002 A1 | 4/1991 |
| EP | 0 542 428 A1 | 5/1993 |
| EP | 0 601 709 A2 | 6/1994 |
| EP | 0 621 008 A2 | 10/1994 |
| EP | 0 696 459 A1 | 2/1996 |
| EP | 1 629 787 A2 | 3/2006 |
| GB | 2327352 A | 1/1999 |
| WO | WO 94/01149 | 1/1994 |
| WO | WO 96/39958 | 12/1996 |
| WO | WO 99/42152 | 8/1999 |
| WO | WO 02/30305 A | 4/2002 |
| WO | WO 2005/009257 A2 | 2/2005 |
| WO | WO 2005/034766 A2 | 4/2005 |

OTHER PUBLICATIONS

International Search Report in International Application No. PCT/GB2007/003270, mailed Nov. 7, 2007, corresponding to related U.S. Appl. No. 11/523,754.

GB Search Report for U.K. Application No. GB 0617600.2, dated Dec. 21, 2006, corresponding to related U.S. Appl. No. 11/523,754.

GB Search Report for U.K. Application No. GB 0617599.6, dated Dec. 21, 2006 corresponding to related U.S. Appl. No. 11/523,807.

International Preliminary Report on Patentability issued in corresponding International Patent Application No. PCT/GB2007/003292 (Date of Completion of Report: Feb. 5, 2009).

Office Action dated Feb. 3, 2009, issued in related U.S. Appl. No. 11/523,754, filed Sep. 20, 2006.

Final Office Action, mailed Jul. 29, 2009 in related U.S. Appl. No. 11/523,754, filed Sep. 20, 2006.

Office Action, mailed Jan. 27, 2010 in related U.S. Appl. No. 11/523,754, filed Sep. 20, 2006.

* cited by examiner

SURGICAL INSTRUMENT

RELATED APPLICATIONS

This application is a continuation-in-part of application Ser. No. 10/924,954, filed Aug. 25, 2004, now abandoned which claims priority to U.K application 0411270.2, filed May 20, 2004, the entire contents of which are hereby incorporated by reference in this application.

BACKGROUND OF THE INVENTION

This invention relates to a bipolar electrosurgical instrument for use in the bulk removal of tissue, as in a laparoscopic hysterectomy.

In a laparoscopic hysterectomy, the body of the uterus is resected from the stump or fundus, and then removed from the operative site. To enable the uterus to be removed through a limited surgical opening, it is desirable to morcellate it into relatively smaller pieces of tissue, which are easier to remove. The present invention relates to an instrument and method for morcellating and removing a uterus.

U.S. Pat. Nos. 5,957,884, 6,007,512 and 6,036,681 are examples of morcellating devices in which an element carrying an electrode is rotated in order to cause the morcellation of tissue. This rotation of the electrode necessitates a mechanical drive arrangement, which increases the complexity of the instrument. The present invention seeks to provide a simpler and hence more reliable arrangement for the bulk removal of tissue.

SUMMARY OF THE INVENTION

Accordingly, there is provided the combination of a device for morcellating tissue within a body cavity of a patient and a tissue-pulling device, the morcellating device comprising a stationary tube having a distal end portion, the tissue-pulling device being locatable within the tube, the combination including a bipolar electrosurgical electrode assembly including first and second electrodes located at the distal end of the tube and separated one from the other by an insulation member, the arrangement being such that when an electrosurgical cutting voltage is applied to the electrode assembly the tissue-pulling device can be moved to pull tissue against the distal end of the tube to form a core of severed tissue within the tube, and further moved in order to remove the severed tissue from the body cavity of the patient.

Conveniently, the electrosurgical electrode assembly extends around the circumference of the distal edge of the tube, preferably completely around the circumferential edge.

U.S. Pat. No. 5,304,124 describes an instrument for removing a myoma from the uterus of a patient, the device utilising a cauterising element at the end of a tubular member. This cauterising element is described as being a wire loop, or a "Bovie-type component". As this device is for the removal of a myoma (leaving the remainder of the uterus intact), the cauterising element will reduce the bleeding from the remainder of the uterus, which will still be vascularly connected to the patient. In contrast, the present invention provides a bipolar electrosurgical device, more suited to the bulk removal of tissue form a uterus which has been resected and will no longer have a vascular supply.

The second electrode of the bipolar assembly is preferably set back axially from the first electrode along the longitudinal axis of the tube. The tube itself conveniently constitutes the first electrode, the second electrode, or the insulation member. In one arrangement, at least one of the electrodes comprises a conductive track present on the insulation member, for example by the printing of the track on the insulation member.

The second electrode is conveniently additionally located on, or constituted by, the tissue-pulling device. With the second electrode located on the tube, if there is no electrical connection between the second electrode and the tissue-pulling device, there will possibly be a situation in which tissue being pulled into the tube is in contact with the first electrode but not the second. Under these circumstances, the electrosurgical cutting of the tissue will not be effected until the tissue is pulled far enough so as to contact the second electrode. By placing the second electrode on the tissue-pulling device, or by making the second electrode in electrical communication with the tissue-pulling device, the cutting of tissue will be effected by a bipolar electrode assembly constituted between the tissue-pulling device and the first electrode.

By providing both a second electrode on the tube, and making the tissue-pulling device effective as the second electrode, each will act as the second electrode at different times. When the tissue is first presented to the tube, the tissue-pulling device will act as the second electrode. Subsequently, as the tissue is pulled into the tube, the bipolar cutting will occur between the first electrode and the second electrode located on the tube. This arrangement ensures that, as the first tissue contact with the tube is established, the bipolar electrode assembly is capable of firing up successfully, and yet continues to be effective as more and more tissue is pulled into the tube.

Thus, it will be seen that the bipolar electrode assembly is constituted by having two electrodes in the distal region of the tube, and additionally an optional electrode on the tissue-pulling device. Either of these arrangements constitute "bipolar" electrode assemblies, even if the tissue-pulling device constitutes an additional electrode. A bipolar electrode assembly has at least two electrodes, manoeuvrable in the immediate region of the surgical site. This is in contrast to monopolar or "Bovie type" arrangements, in which an immovable return pad is attached to the patient at a point somewhat removed from the surgical site.

The tissue-pulling device is preferably longitudinally movable with respect to the tube. By the use of a pulling device, the tube can be maintained stationary and tissue pulled into the end of the tube. There is, therefore, no need to advance the tube or otherwise move it into the tissue to be removed, as with many of the prior art devices.

The tissue-pulling device is preferably a pair of jaw members movable between open and closed positions, the jaw members conveniently being mounted on a rod extending through the tube. The jaws can be closed around tissue, grasping it firmly, and the rod retracted within the tube to cause the tissue to be severed by the electrosurgical electrode assembly at the distal end of the tube. Alternatively, the tissue-pulling device comprises a screw member rotatable with respect to the tube. Rotation of the screw member has the effect of pulling tissue into the tube.

The tube conveniently has an end face which is angled with respect to the longitudinal axis of the tube, preferably at an angle of between 30 and 60 degrees to the longitudinal axis, and typically at 45 degrees thereto. This angled end face helps to ensure that the initial contact between the tissue and the electrode assembly is a point contact, thereby assisting with the firing-up of the electrode assembly into a cutting or vaporisation mode and ensuring effective separation of the tissue.

The stationary tube alternatively has an end face with an undulating circumference, typically a castellated or alternatively a wave-like circumferential surface. In one convenient arrangement, the circumference undulates substantially in the form of a sine wave. These different end profiles each help to provide one or more gradually-progressing point of contact, as opposed to a uniform contact over the whole of the end circumference, thereby assisting with the electrosurgical cutting of tissue.

The first electrode preferably has a distal portion including a plurality of apertures disposed around its circumference, preferably in one or more rows of apertures set back from the end of the tube. The apertures are conveniently circular holes, or alternatively elongate slots, and the apertures in one row are preferably radially offset from the apertures in an adjacent row. The apertures seek to ensure that heat is not conducted away too rapidly from the distal circumference of the first electrode, thereby keeping the active electrode at a high temperature and reducing the rate at which the remainder of the instrument increases in temperature.

The invention also extends to a method of laparoscopically removing a uterus the method comprising the steps of
 a) dissecting the body of the uterus from the stump of the uterus,
 b) laparoscopically inserting a morcellating device comprising a stationary tube having a distal end portion, and a tissue-pulling device located within the tube, the morcellating device and/or the tissue-pulling device including a bipolar electrosurgical electrode assembly, the electrosurgical assembly comprising first and second electrodes located at the distal end of the tube and separated one from the other by an insulation member,
 c) grasping tissue with the tissue-pulling device and pulling it against the distal end of the tube,
 d) energising the bipolar electrode assembly with an electrosurgical cutting voltage,
 e) continuing to pull the tissue with the tissue-pulling device so that a core of tissue is formed within the tube, and
 f) withdrawing the core of tissue from the tube.

Finally, the invention also extends to a device for morcellating tissue within a body cavity of a patient, the device comprising a stationary tube having a distal end portion, and a bipolar electrosurgical electrode assembly located at the distal end of the tube, the electrosurgical assembly comprising first and second electrodes separated by an insulation member, the bipolar electrosurgical electrode assembly extending around the circumference of the distal edge of the tube, such that when an electrosurgical cutting voltage is applied to the electrode assembly and relative movement is initiated between the tube and the tissue, a core of severed tissue is formed within the tube such that it can be removed from the body cavity of the patient.

BRIEF DESCRIPTION OF THE DRAWINGS

The invention will now be described in more detail, by way of example only, with reference to the accompanying drawings, in which.

DESCRIPTION OF PREFERRED EMBODIMENTS

Figure 1:
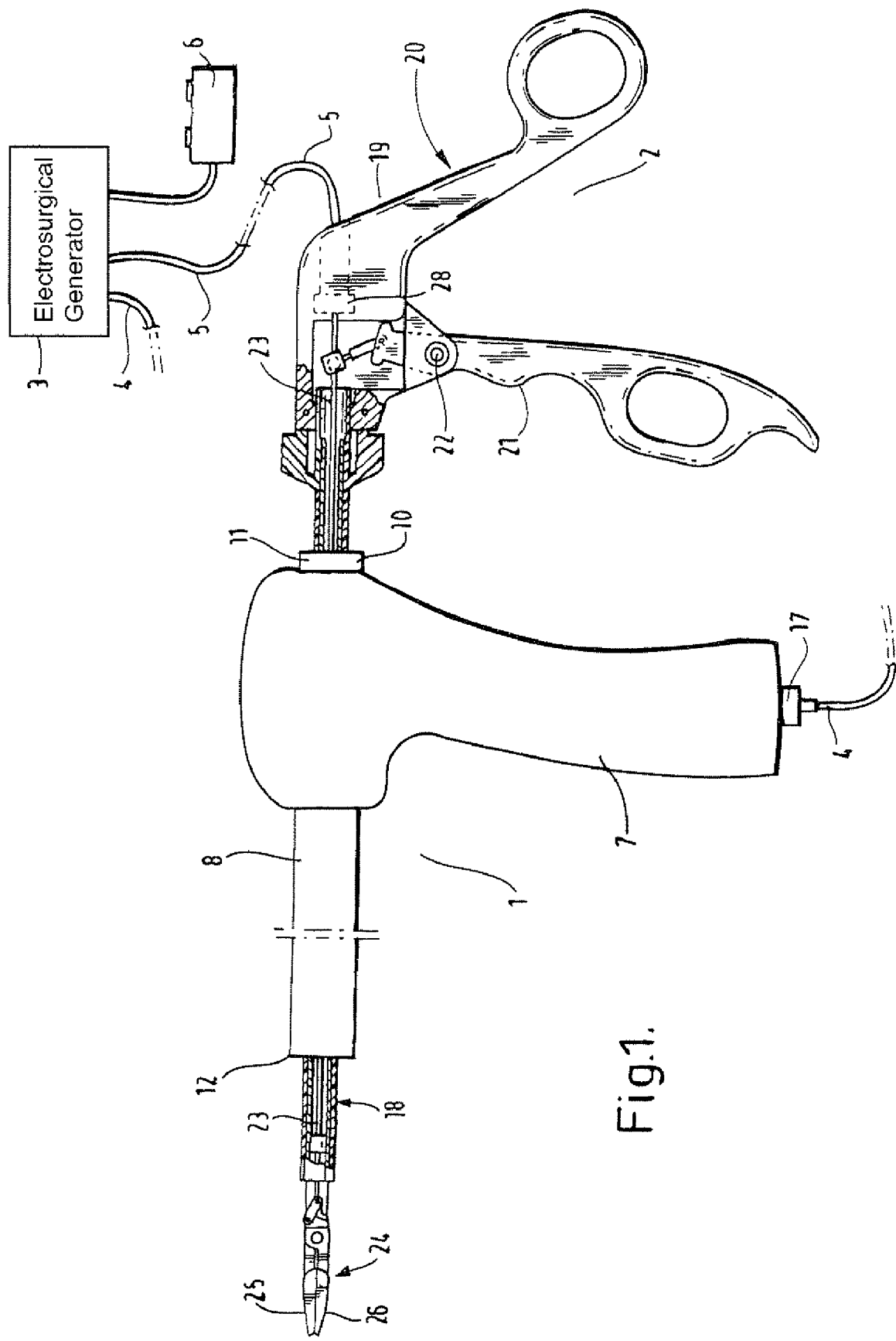
FIG. 1 is a schematic side view, partly in section, of a morcellating system in accordance with the present invention.

Referring to FIG. 1, a morcellating system comprises a morcellating device shown generally at 1, a tissue-pulling device shown generally at 2, and an electrosurgical generator 3. The generator 3 is connected to the morcellating device 1 by means of cable 4, and to the tissue-pulling device 2 by means of cable 5. The generator 3 is controlled by means of footswitch 6.

Figure 2:
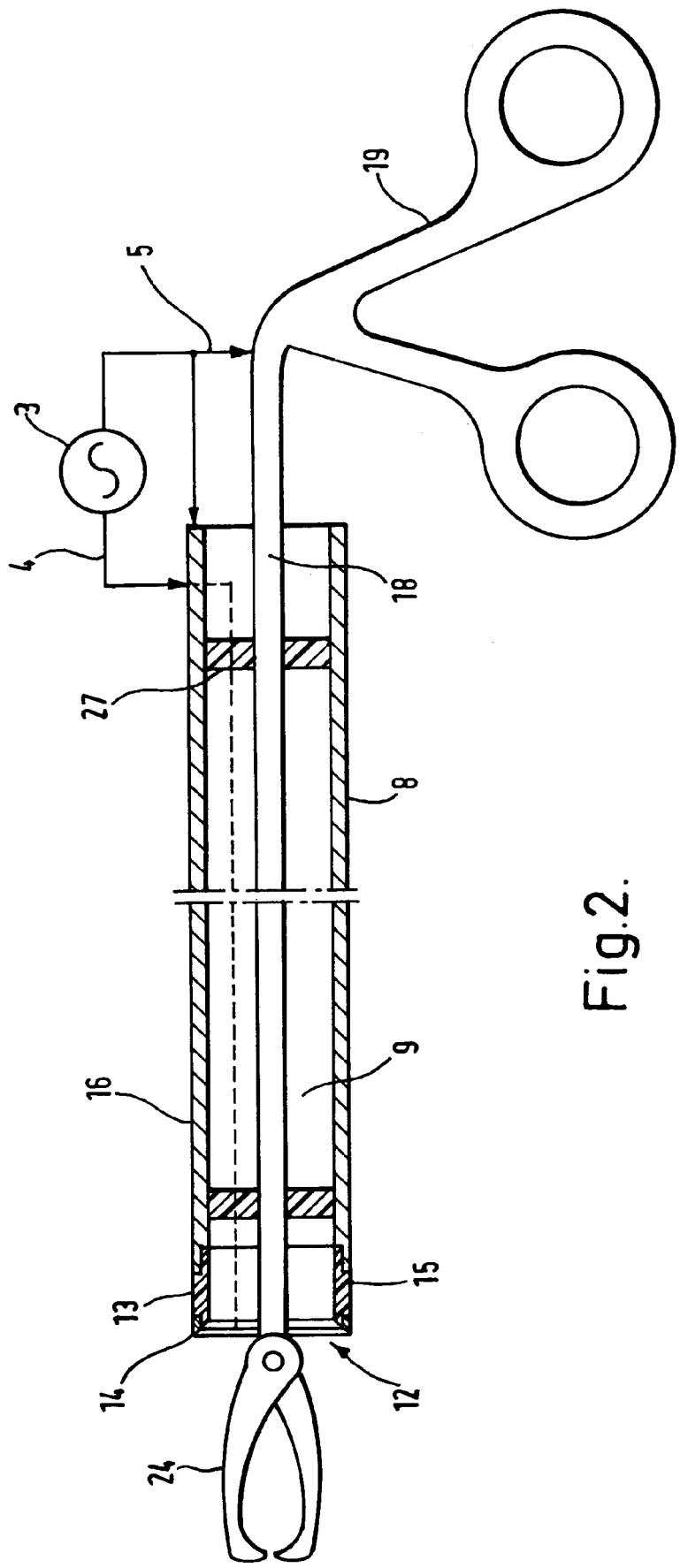
FIG. 2 is a schematic sectional view of a part of the system of FIG. 1, FIGS. 3 to 6 are schematic views of alternative embodiments of the part of FIG. 2, FIGS. 7 and 8 are schematic views of further alternative embodiment of the distal end of the part of FIG. 2, FIGS. 9 and 10 are schematic views of electrodes for use with the part of FIG. 2.

As shown in FIGS. 1 and 2, the morcellating device 1 comprises a handle 7 and a cylindrical tube 8. The cylindrical tube 8 is hollow, and defines a lumen 9 therein. The proximal end 10 of the tube 8 extends from the handle 7 as shown at 11, and the distal end 12 of the tube is provided with an electrosurgical electrode assembly 13. The electrosurgical electrode assembly 13 comprises an active tissue-cutting electrode 14, and an insulation member 15, both extending around the circumference of the tube 8. The insulation member 15 separates the electrode 14 from the remainder of the tube 8, which acts as a return electrode 16.

The tube 8 is connected to one pole of the generator 3, via the cable 4 and a connector 17. The active electrode 14 extends around the entire circumference of the tube 8, and is connected to the other pole of the generator 3, via the cable 4, the connector 17 and additional wiring (not shown). In this way, the electrodes 14 and 16 constitute a bipolar electrode assembly, which, when energised by the generator 3, is capable of cutting tissue coming into contact with the distal end of the tube 8.

The tissue-pulling device 2 comprises a tubular shaft 18, at the proximal end of which is a scissors-type handle mechanism 19, having a first handle 20 and a second handle 21. The second handle 21 is pivotable with respect to the first, about a pivot pin 22.

Pivoting of the second handle 21 causes longitudinal movement of a push rod 23 extending through the shaft 18 to the distal end thereof.

At the distal end of the shaft 18 is a jaw assembly 24, with a first jaw member 25 and a second jaw member 26 movable between open and closed positions by the movement of the push rod 23. The tissue-pulling device 2 is manually translatable in a longitudinal manner within the lumen 9 of the morcellating device 1, with slidable guide members 27 supporting the shaft 18 of the tissue-pulling device within the tube 8. The jaw members 25 and 26 are electrically connected to the shaft 18, and the shaft is electrically connected, via the lead 5 and a connector 28, with the generator 3. The shaft 18 is connected to the same pole of the generator 3 as the return electrode 16, constituted by the tube 8.

The operation of the morcellating system is as follows. The tube 8 of the morcellating device 1 is inserted into the body of a patient, typically through a trocar (not shown), and brought into position adjacent to the tissue to be removed (typically a resected uterus in the case of a laparoscopic hysterectomy). The tissue-pulling device 2 is then inserted through the lumen 9 of the morcellating device 1. The handle 21 is operated to open the jaw assembly 24, and the tissue-pulling device 2 is manoeuvred so that tissue from the uterus is located between the jaw members 25 and 26. The handle 21 is then operated to close the jaw assembly 24, grasping tissue therein.

The surgeon operates the footswitch 6 to operate the generator 3 so that an electrosurgical cutting voltage is supplied between the tissue-cutting electrode 14 and the return electrode 16. As mentioned previously, the push rod 23 and the jaw assembly 24 are also electrically connected to the same pole of the generator 3 as the tube 8, and so both the tube and the jaw assembly constitute the return electrode 16. With tissue firmly grasped in the jaw assembly 24, the device 2 is slowly withdrawn from the tube 8, pulling the tissue against the distal end of the tube and the tissue-cutting electrode 14. As the tissue contacts the tissue-cutting electrode 14, it is vaporised, allowing the device 2 to be withdrawn further into the tube 8. In this way, a cylindrical core of tissue is formed in the tube 8, the tissue being withdrawn though the proximal end 10 of the morcellating device 1 (which remains outside the body of the patient) for disposal.

The tissue-pulling device 2 can then be re-inserted into the tube 8 such that a further core of tissue can be removed from the body of the patient. By repeating this process, large quantities of tissue can be removed from the patient in a relatively short time, such that the entire uterus can be removed, if necessary, while still employing a laparoscopic approach.

Figure 3:
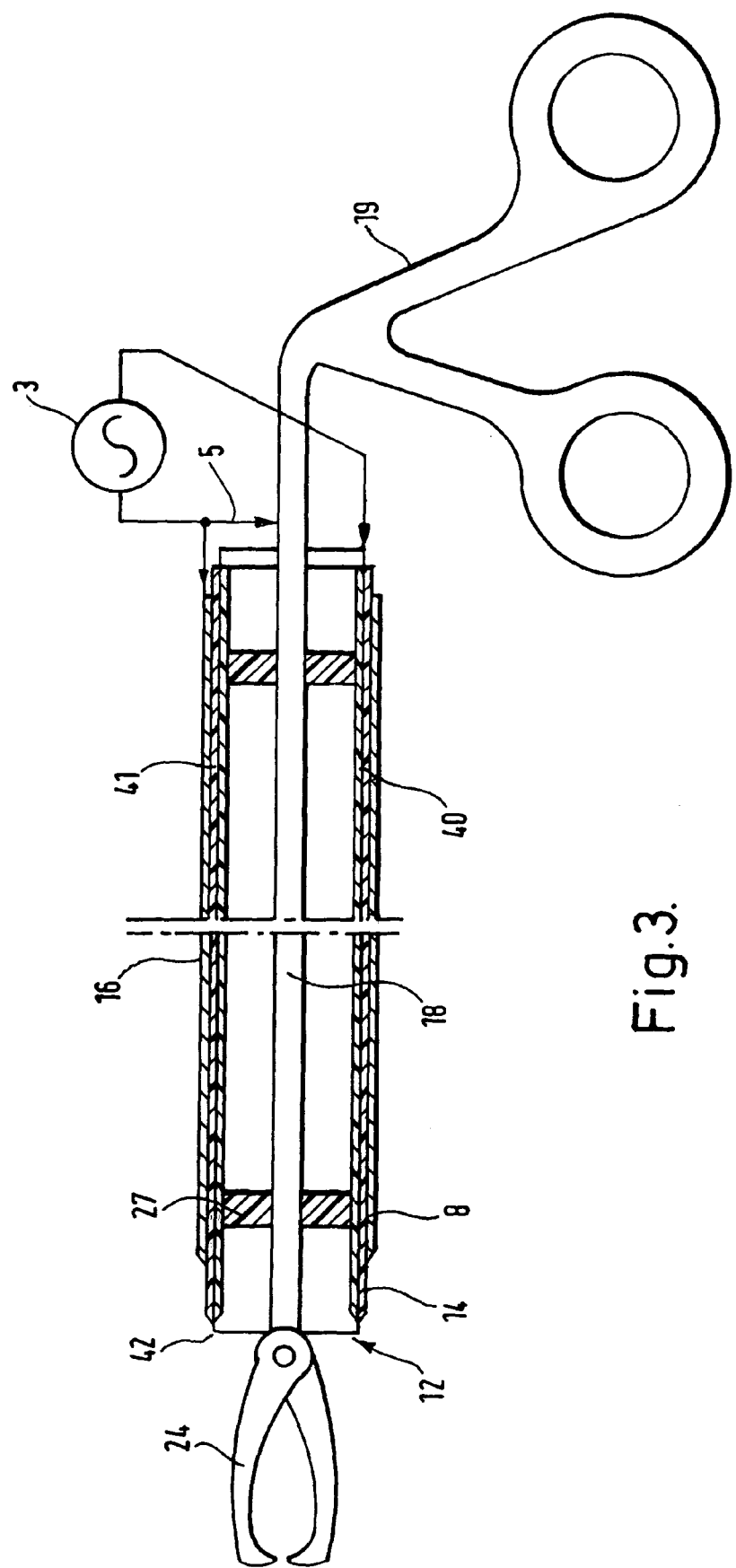

In the instrument described above, the tube 8 provides the return electrode 16 (or in other words, the return electrode provides the structural integrity of the tube). FIG. 3 shows an alternative embodiment in which the active electrode 14 provides the structural element of the tube 8. The tube 8 is covered on its inner surface by a layer 40 of insulating material, typically of ceramic or a polymer material such as nylon or silicone rubber. The tube 8 is similarly covered on its outer surface by a layer 41, also of an insulating nylon or silicone rubber material. The insulating layers 40 and 41 stop just short of the distal end 12 of the tube 8, leaving an exposed area 42 constituting the exposed active electrode 14. A further deposited layer of conductive material (such as copper coated with a biocompatible material such as gold or silver) constitutes the return electrode 16.

The instrument operates in similar fashion to that described with reference to FIGS. 1 and 2, with the tissue-pulling device 2 grasping tissue and pulling it against the distal end 12 of the tube 8, where it is vaporised by the current flowing between the active tissue-cutting electrode 14 and the return electrode 16.

Figure 4:
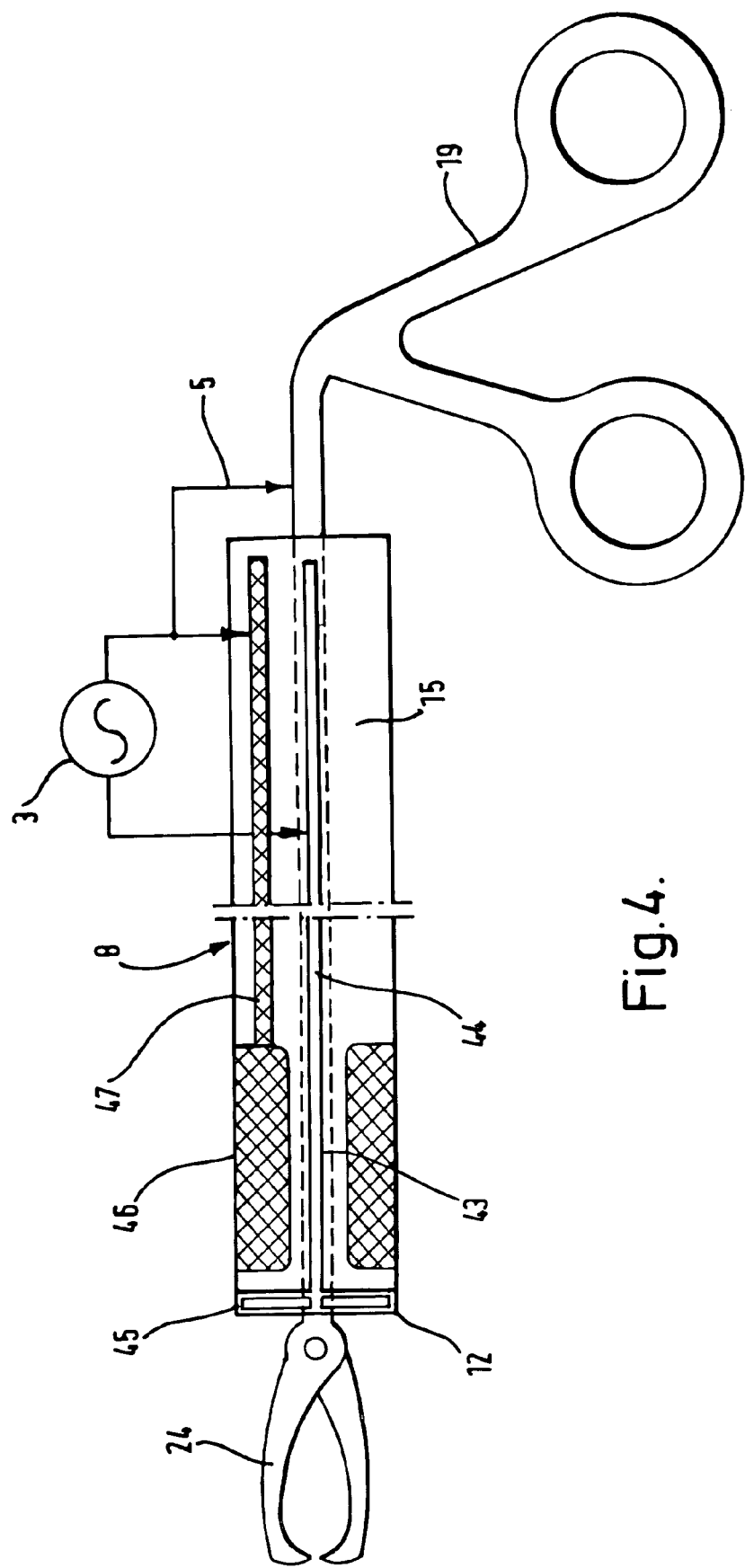

FIG. 4 shows an alternative embodiment in which the structural integrity of the tube 8 is provided by the insulation member 15. The tube 8 is formed of a rigid ceramic or glass-reinforced nylon material, and has a metallic insert 43 attached thereto. The insert 43 has one or more longitudinal struts 44 extending the length of the tube 8. The struts 44 serve as leads for the electrosurgical current from the generator 3, and also as supports for a circumferential active electrode structure 45 at the distal end 12 of the tube 8. The tube 8 is also coated with a metallic material such as copper to form a return electrode 16. Unlike the construction shown with respect to FIG. 3, the metallic coating in the embodiment of FIG. 4 provides discrete return pads 46, and a lead 47. The return electrode structure can be provided on the inner surface of the tube 8, on the outer surface, or on both inner and outer surfaces.

The operation is again as previously described, with tissue being pulled against the distal end 12 of the tube 8, to be vaporised by the current flowing between the active and return electrodes 14 and 16.

Figure 5:
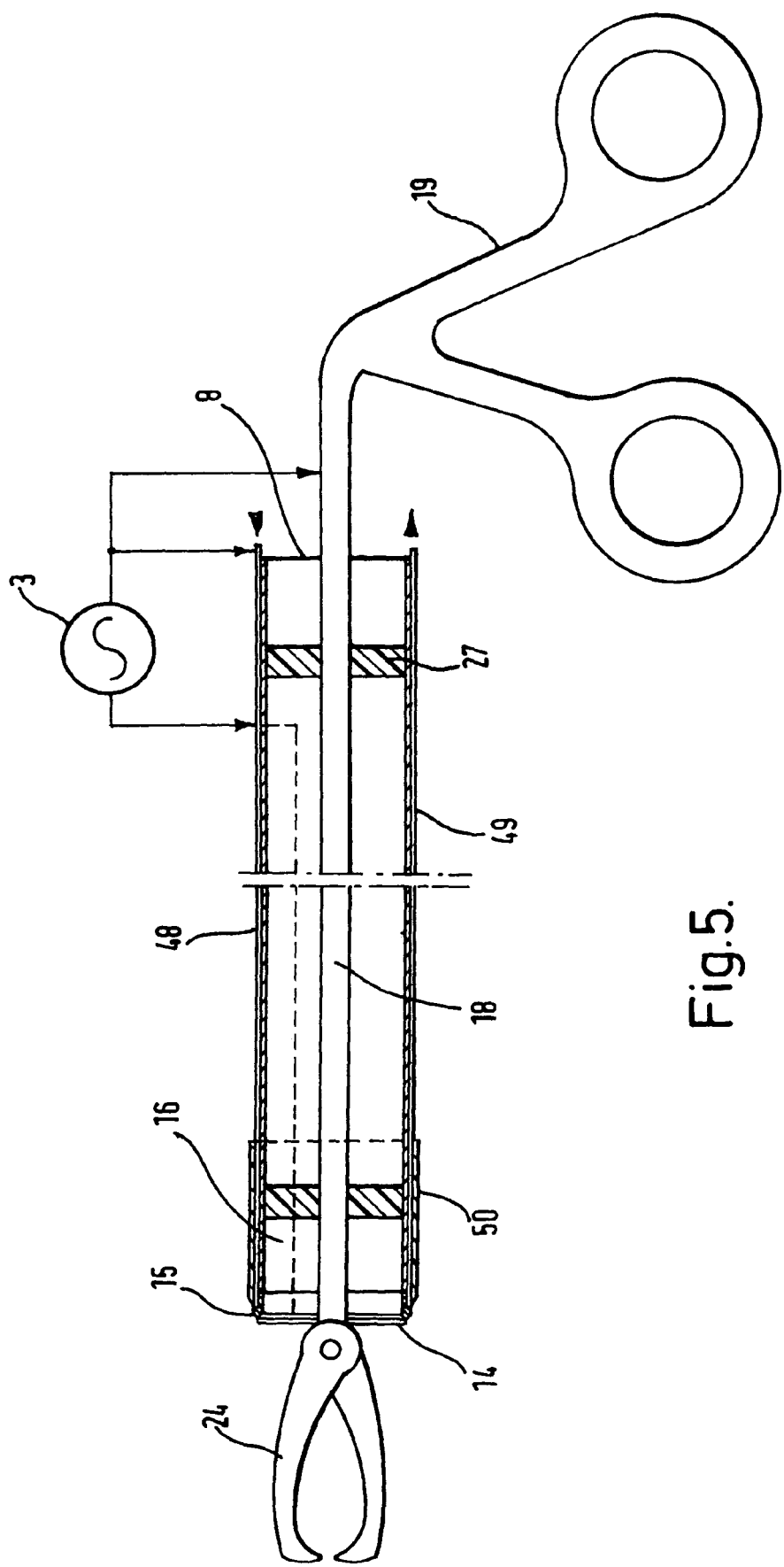

FIG. 5 shows an alternative embodiment in which a cooling system is provided to ensure that the return electrode 16 does not reach an excessive temperature. The overall construction is similar to that of FIG. 2, with previously described components being given the same reference numerals, and the return electrode 16 constituting the structural integrity of the tube 8. In addition to the tube 8, there is provided a fluid inlet pipe 48, a fluid outlet pipe 49 and a cooling jacket 50. The cooling jacket 50 surrounds the distal portion of the tube 8, while leaving the extreme distal end 12 exposed so that the active electrode 14 can contact tissue being pulled into the tube. Cooling fluid is pumped through the cooling jacket 50, and transfers heat away from the distal end of the return electrode 16. This ensures that the distal end of the return electrode 16 does not reach a temperature at which tissue adheres thereto.

Figure 6:
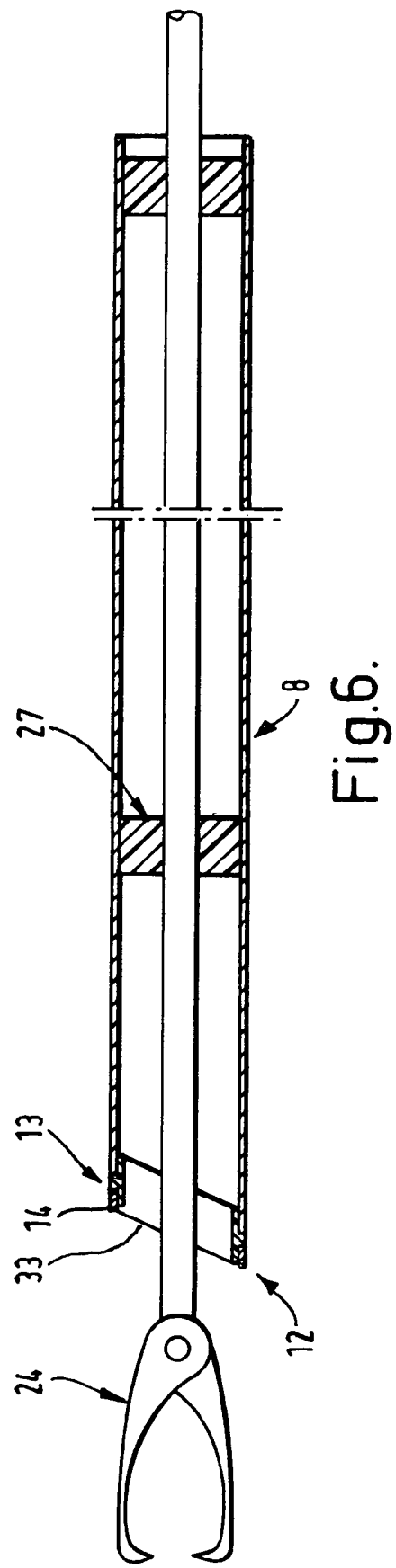

FIG. 6 shows an alternative embodiment of the tube 8, in which the distal end 12 of the tube has an angled end, as shown at 33. This angled end 33, which typically lies at an angle of 45 degrees to the longitudinal axis of the tube 8, helps to provide an initial point contact between the tissue-cutting electrode 14 and the tissue being drawn into the tube. This assists in ensuring effective electrosurgical cutting of the tissue.

Figure 7:
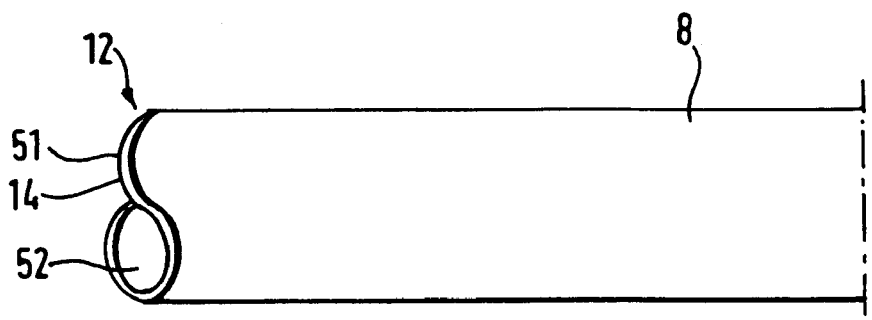

FIG. 7 shows an alternative construction in which the distal end 12 of the tube 8 has an undulating circumference. The undulating circumference is in the form of a sine wave with peaks 51 and troughs 52. Although the construction of FIG. 7 is shown with two peaks 51 and two troughs 52, constructions with other numbers of peaks and troughs are also envisaged. The undulating circumference of the end of the tube 8, which constitutes the active tissue-cutting electrode 14, ensures that the active electrode contacts the tissue at one or more point contact positions, thereby assisting in ensuring effective tissue separation.

Figure 8:
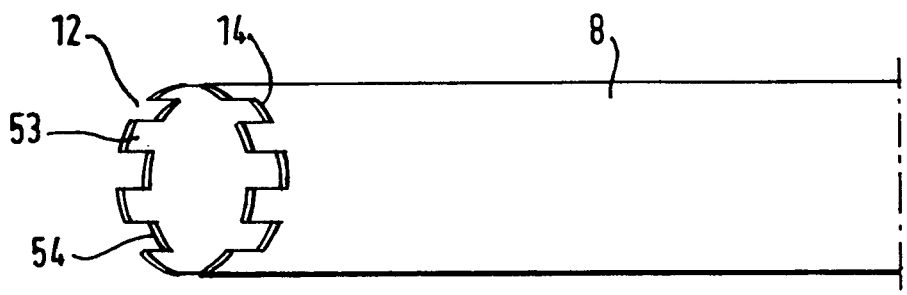

FIG. 8 shows a further embodiment of the tube in which the distal end of the tube 8 is in a castellated form, with protrusions 53 and recesses 54. Once again, this ensures that the tissue-cutting electrode 14 makes contact with the tissue at a plurality of discrete locations around the circumference of the tube 8.

Figure 9:
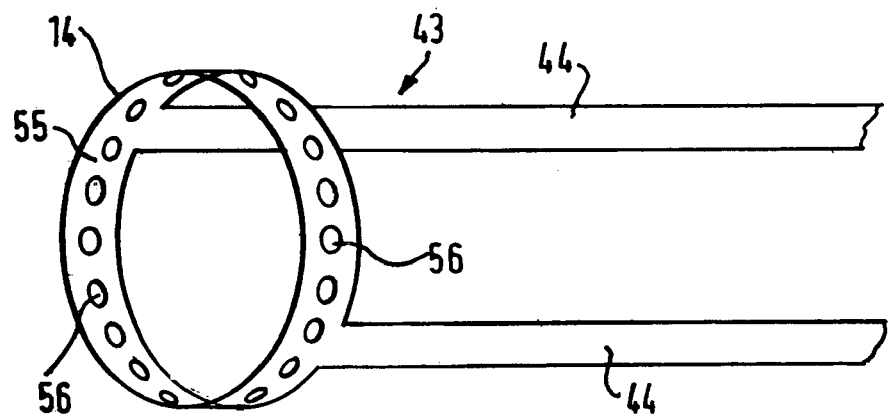

FIG. 9 shown a design of active tissue-cutting electrode 14. The electrode is in the form of a ring 55, supported by two struts 44 as previously described with reference to FIG. 4. The ring 55 is provided with a plurality of circular holes 56 extending radially around the ring 55. The holes 56 help to reduce the conduction of heat, generated by the tissue-cutting electrode 14, to other proximal components of the instrument, such as the insulation member 15 or the return electrode 16. This assists in maintaining the active electrode 14 at a high temperature for cutting tissue, while preventing the return electrode 16 from reaching an excessive temperature at which tissue will start to adhere to that electrode. Although the ring 55 is shown in FIG. 8 with a plain circular circumference, the holes 56 can equally be employed with the irregular-shaped constructions shown in FIGS. 7 and 8.

Figure 10:
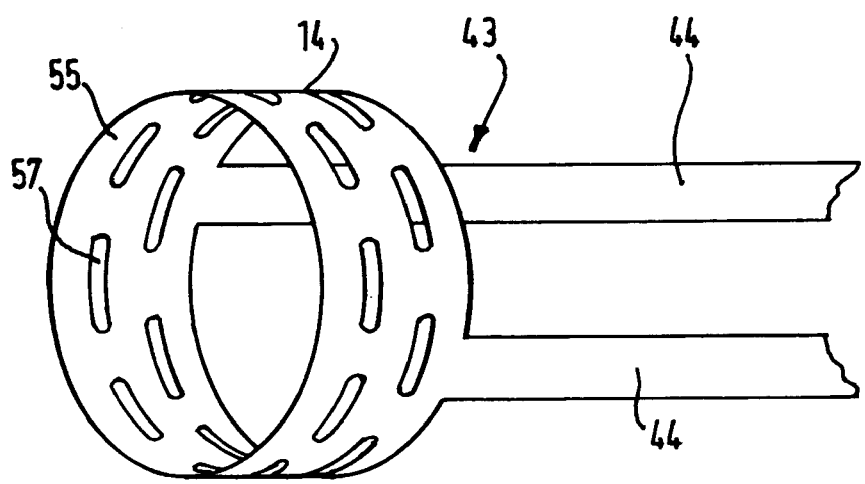

Furthermore, the holes 56 can be replaced by slots 57, as shown in FIG. 10. FIG. 10 shows an active electrode 14 in the form of a ring 55 with two staggered rows of slots 57. The staggering of the rows also helps to prevent heat generated by the active electrode 14 being passed in a proximal direction to the other components of the instrument.

Figure 11:
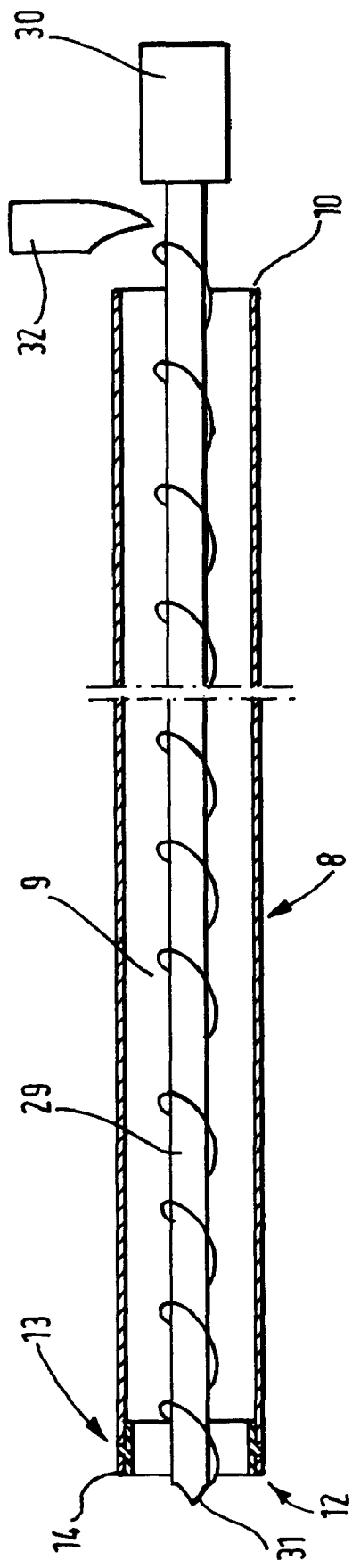
FIG. 11 is a schematic sectional view of an alternative embodiment of morcellating system constructed in accordance with the present invention.

Finally, FIG. 11 shows the tube 8 of an alternative embodiment of morcellating device 1, in which the tissue-pulling device 2 is constituted by a screw-member 29. The screw-member 29 is rotatably driven at its proximal end by means of a motor 30, and has a sharp tip 31 at its distal end. The tip 31 of the screw-member 29 engages tissue, and the rotation of the screw-member causes the tissue to be pulled against the distal end of the tube 8, where it is vaporised by the electrosurgical electrode assembly 13 as previously described. Tissue travels up the tube 8 under the action of the rotation of the screw-member 29, until it exits from the proximal end 10 of the tube, to be removed from the screw-member by a stripping element 32. This arrangement has the advantage that the extraction of tissue can be effected on an almost continuous basis, without the need for the removal and re-insertion of the tissue-pulling device of the previous Figures.

Those skilled in the art will appreciate that, in addition to the jaw device and screw-member described above, other means for pulling tissue into the tube 8 can be envisaged. The bipolar electrosurgical assembly 13 will be capable of cutting tissue pulled into contact therewith, by any suitable means.

What is claimed is:

1. A device comprising an electrosurgical system for morcellating tissue within a body cavity of a patient, the system comprising:
    an electrosurgical generator,
    a morcellating device, and
    a tissue-pulling device,
    the morcellating device comprising:
        a tube having a distal end,
            a bipolar electrosurgical electrode assembly including first and second electrodes located at the distal end of the tube and separated one from the other by an insulation member, and
            first and second connections by which the first and second electrodes are connected to the electrosurgical generator,
        the tissue-pulling device being locatable within the tube, and including a third connection by which the tissue-pulling device is connected to the electrosurgical generator so that the tissue-pulling device is an additional electrode,
        the electrosurgical generator supplying an electrosurgical cutting voltage to the electrode assembly, such that when the tissue-pulling device is moved to pull tissue against the distal end of the tube, the electrosurgical cutting voltage supplied to the bipolar electrosurgical electrode assembly and/or tissue pulling device severs the tissue to form a core of tissue within the tube, which can then be further moved in order to remove the severed tissue from the body cavity of the patient.

2. The device according to claim 1, wherein the tube has a distal edge, and the first electrode extends around the circumference of the distal edge of the tube.

3. The device according to claim 2, wherein the first electrode extends completely around the circumference of the tube.

4. The device according to claim 1, wherein the second electrode is set back axially from the first electrode along the longitudinal axis of the tube.

5. The device according to claim 1, wherein the tube constitutes the first electrode.

6. The device according to claim 5, wherein at least one of the electrodes comprises a conductive track present on the insulation member.

7. The device according to claim 6, wherein the conductive track is printed on the insulation member.

8. The device according to claim 1, wherein the tube constitutes the second electrode.

9. The device according to claim 1, wherein the tube constitutes the insulation member.

10. The device according to claim 1, wherein the tissue-pulling device is longitudinally movable with respect to the tube.

11. The device according to claim 10, wherein the tissue-pulling device comprises a pair of jaw members movable between open and closed positions.

12. The device according to claim 11, wherein the jaw members are mounted on a rod extending though the tube.

13. The device according to claim 1, wherein the tissue-pulling device comprises a screw member rotatable with respect to the tube.

14. The device according to claim 1, wherein the tube has an end face which is angled with respect to the longitudinal axis of the tube.

15. The device according to claim 14, wherein the end face of the tube is at an angle of between 30 and 60 degrees to the longitudinal axis of the tube.

16. The device according to claim 15, wherein the end face of the tube is at an angle of 45 degrees to the longitudinal axis of the tube.

17. The device according to claim 1, wherein the tube has an end face with an undulating circumference.

18. The device according to claim 17, wherein the end face has a castellated circumference.

19. The device according to claim 17, wherein the end face has a circumference that undulates in a wave-like manner.

20. The device according to claim 19, wherein the end face has a circumference that undulates substantially in the form of a sine wave.

21. The device according to claim 1, wherein the first electrode has a distal portion including a plurality of apertures disposed around its circumference.

22. The device according to claim 21, wherein the apertures are in the form of circular holes.

23. The device according to claim 21, wherein the apertures are in the form of elongated slots.

24. The device according to claim 21, wherein the distal portion includes a plurality of rows of apertures.

25. The device according to claim 24, wherein the apertures in one row are radially offset from the apertures in an adjacent row.

26. A device comprising an electrosurgical system for morcellating tissue within a body cavity of a patient, the morcellating device comprising:
    an electrosurgical generator,
    a morcellating device, and
    a tissue-pulling device,
    the morcellating device comprising:
        a stationary tube having a distal end,
        a bipolar electrode assembly including first and second electrodes located at the distal end of the tube, the first electrode being an active electrode, and the second electrode being a return electrode,
        an insulation member positioned so as to separate the first and second electrodes from one another, and
        first and second cables for connecting the first and second electrodes to first and second poles, respectively, of the electrosurgical generator,
    the tissue-pulling device being locatable within the tube and including:
        a pair of jaw members movable between open and closed positions, and
        a third cable for connecting the jaw members to the first or second pole of the electrosurgical generator so that the jaw members are, together, an additional, third electrode,
    wherein, when an electrosurgical cutting voltage is applied to the electrode assembly and/or tissue-pulling device, the tissue-pulling device can be moved to pull tissue against the distal end of the tube so that the first, second and/or third electrodes sever the tissue to form a core of severed tissue within the tube, and further moved to remove the severed tissue from the body cavity of the patient.

* * * * *